US012808067B2

(12) United States Patent
Şahin et al.

(10) Patent No.: US 12,808,067 B2
(45) Date of Patent: Nov. 24, 2026

(54) METHOD FOR PRODUCING PHTHALOCYANINE GRAPHENE HYBRID MATERIALS

(71) Applicants: YILDIZ TEKNİK ÜNİVERSİTESİ, Esenler (TR); YILDIZ TEKNOLOJI TRANSFER OFISI ANONIM SIRKETI, Esenler (TR)

(72) Inventors: Yücel Şahin, Istanbul (TR); Hürmüs Gürsu, Istanbul (TR); Özge Koyun, Istanbul (TR); Semih Gördük, Istanbul (TR)

(73) Assignees: YILDIZ TEKNIK ÜNIVERSITESI, Esenler (TR); YILDIZ TEKNOLOJI TRANSFER OFISI ANONIM SIRKETI, Esenler (TR)

( * ) Notice: Subject to any disclaimer, the term of this patent is extended or adjusted under 35 U.S.C. 154(b) by 619 days.

(21) Appl. No.: 18/556,492

(22) PCT Filed: Mar. 31, 2022

(86) PCT No.: PCT/TR2022/050282
§ 371 (c)(1),
(2) Date: Oct. 20, 2023

(87) PCT Pub. No.: WO2022/225488
PCT Pub. Date: Oct. 27, 2022

(65) Prior Publication Data

US 2024/0191367 A1 Jun. 13, 2024

(30) Foreign Application Priority Data

Apr. 20, 2021 (TR) .............................. 2021/006873

(51) Int. Cl.

| | |
|---|---|
| ***C25B 3/29*** | (2021.01) |
| ***C01B 32/184*** | (2017.01) |
| ***C01B 32/198*** | (2017.01) |
| ***C01B 32/23*** | (2017.01) |
| ***C07D 487/22*** | (2006.01) |
| ***C25B 1/135*** | (2021.01) |
| ***C25B 3/09*** | (2021.01) |
| ***C25B 11/043*** | (2021.01) |
| *H01G 11/32* | (2013.01) |
| *H01G 11/86* | (2013.01) |

(52) U.S. Cl.
CPC .............. *C25B 3/29* (2021.01); *C01B 32/184* (2017.08); *C01B 32/198* (2017.08); *C01B 32/23* (2017.08); *C07D 487/22* (2013.01); *C25B 1/135* (2021.01); *C25B 3/09* (2021.01); *C25B 11/043* (2021.01); *C01B 2204/22* (2013.01); *H01G 11/32* (2013.01); *H01G 11/86* (2013.01)

(58) Field of Classification Search
None
See application file for complete search history.

(56) References Cited

FOREIGN PATENT DOCUMENTS

| | | |
|---|---|---|
| CN | 103818898 A | 5/2014 |
| KR | 101930136 B1 | 12/2018 |

OTHER PUBLICATIONS

Ejigu et al, Single Stage Simultaneous Electrochemical Exfoliation and Functionalization of Graphene, ACS Applied Materials & Interfaces, vol. 9, No. 1, Dec. 2016, pp. 710-721 (Year: 2016).*
Gorduk et al, Fabrication of Tetra-Substituted Copper(II) Phthalocyanine-Graphene Modified Pencil Graphite Electrode for Amperometric Detection of Hydrogen Peroxide, ECS Journal of Solid State Science and Technology, vol. 9, No. 6, Jul. 2020, pp. 1-8 (Year: 2020).*
Greenwood et al, Covalent Modification of Graphene and Graphite Using Diazonium Chemistry: Tunable Grafting and Nanomanipulation, ACS Nano, vol. 9, No. 5, Apr. 2015, pp. 5520-5535 (Year: 2015).*
Lou et al, One-step electrochemical synthesis of tunable nitrogen-doped graphene, Journal of Materials Chemistry A, vol. 4, No. 4, Jan. 2016, pp. 1233-1243 (Year: 2016).*
(Continued)

*Primary Examiner* — Harry D Wilkins, III
(74) *Attorney, Agent, or Firm* — Fresh IP PLC; Clifford D. Hyra; Aubrey Y. Chen

(57) ABSTRACT

Disclosed is a method for producing phthalocyanine-graphene hybrid materials which are covalently bonded by one step and one-pot electrochemical method. The method allows production in one step and does not require a purification procedure. The method includes the process steps of preparing an electrolyte solution having a phthalocyanine compound desired to be obtained simultaneously on a surface of the graphite working electrode, immersing the graphite working electrode into the electrolyte solution, performing a positive potential scanning on the graphite working electrode, converting the graphite working electrode into graphene oxide, converting the graphene oxide into the graphene, bonding the phthalocyanine compound to the graphene covalently in a potential working range scanned simultaneously and enhancing the bonding during the ongoing cycles, obtaining the covalently bonded phthalocyanine-graphene hybrid material obtained based on the applied potential range on the electrode surface, or depositing in solution in powder form.

12 Claims, No Drawings

(56) References Cited

OTHER PUBLICATIONS

Mensing et al, Facile preparation of graphene-metal phthalocyanine hybrid material by electrolytic exfoliation, Journal of Materials Chemistry, vol. 22, No. 33, Jul. 2012, pp. 17094-17099 (Year: 2012).*
Ossonon et al, Functionalization of graphene sheets by the diazonium chemistry during electrochemical exfoliation of graphite, Carbon, vol. 111, Jan. 2017, pp. 83-93 (Year: 2017).*
Pakapongpan et al, Highly selective electrochemical sensor for ascorbic acid based on a novel hybrid graphene-copper phthalocyanine-polyaniline nanocomposites, Electrochimica Acta, vol. 133, Apr. 2014, pp. 294-301 (Year: 2014).*
International Search Report and Written Opinion for International Application No. PCT/TR2022/050282, mailed Sep. 8, 2022.
Gorduk et al. (2020). Electrochemical fabrication and supercapacitor performances of metallo phthalocyanine/functionalized-multiwalled carbon nanotube/polyaniline modified hybrid electrode materials. Journal of Energy Storage, Jan. 2021, vol. 33.

* cited by examiner

METHOD FOR PRODUCING PHTHALOCYANINE GRAPHENE HYBRID MATERIALS

TECHNICAL FIELD

This disclosure describes production of covalently interacting phthalocyanine-graphene hybrid materials in one step and in situ by an electrochemical method, which are used in medicine, electronic devices, opto-electronics and sensor technologies, especially in energy storage systems, and appeal to many markets. The materials developed by a method of the disclosure may be used in components for supercapacitor, battery and battery systems, which are applied in the energy field. It may also be used as a material (as a modifying agent) and electrode component for the detection of the analytes which are important for human and environmental health, for the sensor application field in the health and food industry.

BACKGROUND

Graphene-based materials (graphene, reduced graphene, graphene containing functional groups and graphene oxide) may now be used in many fields, especially in energy storage, sensors, electronic devices. Graphene-based materials will have a plurality of novel and important characteristics such as a higher conductivity, selectivity, stability, etc. when they are functionalized with various macro-compounds and their hybrids are obtained.

In the state of the art, in the production methods used in the literature, graphene-based materials obtained by different methods (such as chemical vapor deposition, chemical and electrochemical exfoliation) are mixed with the phthalocyanine compounds for a long time in the presence of various chemicals (such as dimethyl formamide (DMF), dichlorobenzene (DCB), tetrahydrofuran (THF)), filtered and washed (in the solvents such as ethanol, methanol, dichloromethane), thereby synthesizing a hybrid material. Similarly, a covalent interaction takes place between graphene and phthalocyanine compounds as a result of the functionalization (such as —COOH) of graphene with chemicals such as dicyclohexylcarbodiimide (DCC) by pretreatments. That is, two products obtained by more than one synthesis process are subjected to a production process again for the formation of a hybrid material, and the final product, the hybrid material, is obtained. When the hybrid materials prepared for this purpose are desired to be used as a sensor, they are generally prepared by dripping onto a glassy carbon electrode surface. In these processes, firstly, graphene and phthalocyanine compounds are dissolved in harmful organic solvents such as DMF, they are dripped on an electrolyte surface respectively, and dried, so that they may be used as an electrode material.

The following applications and publications may be considered among the results obtained in the patent and literature search carried out to see the state of the art. The application for Chinese patent register with the publication no. CN111521653 (A) entitled "Tetrahydroxy phthalocyanine zinc-reduced graphene oxide nano-composite as well as electrochemical sensor prepared from the same and application thereof" discloses a method of preparation for the tetrahydroxyphthalocyanine zinc-reduced graphene oxide nano-composite. In the specific preparation method, 0.01 g of tetrahydroxyphthalocyanine zinc is dissolved in 300 μL of DMF and 10 mL 1 mg/mL are added for the reduction. The graphene oxide solution is stirred at room temperature for 12 hours and centrifuged. The precipitate obtained is washed with water in order to obtain tetrahydroxy phthalocyanine zinc-reduced graphene oxide nano-composite, and the tetrahydroxy phthalocyanine zinc-reduced graphene oxide nano-composite obtained is dissolved in 10 mL of water. In this way, the tetrahydroxy phthalocyanine zinc-reduced graphene oxide nano-composite solution is obtained for use. As seen in this method, multiple process steps exist in the production method, such as dissolution, stirring, centrifugation, harmful organic solvents-chemicals are used, such as DMF, and a need for additional washing processes poses a problem.

Furthermore, the Chinese application document with the publication no. CN104091959 (A) discloses an alternative method for preparing a nitro ferrous phthalocyanine-graphene composite material. The object of the invention is to produce a nitro ferrous phthalocyanine-graphene composite material with a high catalytic activity and a catalytic stability against oxygen. Unlike embodiments of the invention in this application, the nitro ferrous phthalocyanine forms a nanosphere structure on a surface of the graphene layer. Furthermore, rinsing with acetone and ethanol and use of DMF are processes involved in the production method. Therefore, it is thought that it does not exceed the above-mentioned technical problems.

The article on the link https://www.researchgate.net/publication/232286950_Facile_preparation_of_graphene-metal_phthalocyanine_hybrid_material_by_electrolytic_exfoliation, another document encountered in the state of the art, discloses a preparation method of a stable aqueous dispersion of the graphene metal phthalocyanine hybrid material by an electrochemical method in the study. In this study, the material was prepared with an electrolyte exfoliation of the graphene in an electrolyte comprising copper phthalocyanine 3,4',4'',4'''-tetrasulfonic acid tetrasodium salt (TSCuPc). Therefore, the electrolyte exfoliation, a different alternative method, was used.

In the literature, there exists various methods for preparing powder phthalocyanine-graphene hybrid materials containing covalent bonds. However, the existing methods which are currently in use and provided above substantially limit the use of these compounds as they have problems such as the existing methods requiring multiple synthesis steps, as well as use of environmentally harmful chemicals, a need for high temperature environment in different methods, and very high economic costs. Thus, the production of the covalently interacting phthalocyanine-graphene hybrid materials in one step and in situ by an electrochemical method at room temperature with environmentally friendly, inexpensive and simple methods is important for the development of widespread use of these materials.

When the covalently interacting phthalocyanine-graphene hybrid materials are used as electrolyte materials, the obtained phthalocyanine-graphene-based hybrid material is attached to any other electrode surface, limiting its production and use as it requires an additional processing step.

As may be seen, current synthesis methods are environmentally harmful, involve multiple reaction steps, and also require high costs. For these reasons, there is a need for a new method for synthesizing covalently interacting phthalocyanine-graphene hybrid materials at room temperature using environmentally friendly, inexpensive and simple methods.

As the production processes of the phthalocyanine-graphene-based materials comprise multiple process steps, there is a need for the production of the covalently bonded phthalocyanine-graphene hybrid materials in a newer, easier, cheaper, more environmentally friendly way, most importantly in one step and in situ. In all the methods used before embodiments of the invention, the production of the phthalocyanine-graphene hybrid materials involves multiple steps, thereby requiring a long process.

Embodiments of the invention make it possible to produce hybrid materials in one step using electrochemical methods by the phthalocyanine compounds present in the solution environment being added simultaneously to the graphene structure by a covalent interaction during graphene formation from the carbon-based materials (graphite, etc.).

SUMMARY

An object of embodiments of this invention is to produce covalently interacting phthalocyanine-graphene hybrid materials by an electrochemical method, which is environmentally friendly and inexpensive, allows one-step and one-pot production and does not require purification procedures.

Another object of embodiments of the invention is to overcome the problems, such as the necessity of obtaining with more than one process step (mechanical stirring, more than one synthesis reaction, dripping process, etc.), additional techniques for removing the chemicals included in the medium during production, a need for labor force and expertness, and high costs, which are encountered in the earlier methods provided in the state of the art above and the methods known in the market. Owing to the production method of embodiments of the invention, no additional process steps are needed, a purification process is not needed, and only a washing process with ultra pure water is applied, as the production process is performed by an electrochemical method in one step and simultaneously. In addition, the fact that it is a simple and inexpensive application is one of the indirect advantages thereof.

Embodiments of the invention provide a direct solution for the preparation of the covalently bonded phthalocyanine-graphene based hybrid materials from the graphite based materials in one step. By embodiments of this invention, the phthalocyanine compound was bound to the graphene electrode and powdery material which were obtained on the surface of the graphite material, by a covalent bond directly in one step using an electrochemical method in one step and simultaneously.

Differently from the state of the art, the phthalocyanine-graphene electrode and powder phthalocyanine-graphene hybrid material are produced from the graphite electrode by the electrochemical method in one step.

An important advantage of the production method of embodiments of the invention is that no additional purification procedure is needed. In addition, use of the environmentally harmful chemicals is not needed.

Another feature is that the phthalocyanine-graphene based hybrid material of higher quality (low defect ratio) is possible to be produced owing to the production method.

The production method developed is a method which is user-friendly, and does not require any expert personnel.

Unlike the state of the art, a production system with an electrode is used in the method studied. Reference electrodes such as Ag/AgCl, calomel, $Hg/HgSO_4$, a Pt counter electrode and graphite based electrodes are used as a working electrode. Solutions comprising mono-protic, poly-protic acids, salts, bases having different functional groups in the structure thereof and the mixture thereof at a concentration range of 0.0001M-5.0 M and the phthalocyanine compounds in a concentration range of 0.000001 M-3.0M are used as an electrolyte.

Unlike the literature, the voltage values used are low and the energy applied is lower, for the graphene production by the electrochemical method. In the related production method, the working potential is in the range of (−3.0 V)−(+6.0 V), the value of the scan rate is in the range of 0.001 V/s−1.0 V/s, and the number of cycles is in the range of 1-500.

Embodiments of the invention, depending on the intended object, allow the phthalocyanine-graphene hybrid materials to be synthesized in a covalently bonded and controlled manner during the formation of the graphene from different phthalocyanine compounds and a graphite material. As may be seen, the preparation of the covalently bonded phthalocyanine-graphene hybrid materials includes an easy, inexpensive, environmentally friendly and user-friendly method.

DETAILED DESCRIPTION

The disclosure relates to a method for producing phthalocyanine-graphene hybrid materials which are covalently bonded by one step and one-pot electrochemical method, wherein the method allows production in one step and does not require a purification procedure.

Embodiments of the invention comprise a method for producing a phythalocyanine-graphene hybrid material in one step in which an electrochemical cyclic voltammetry system comprising a potentiostat allowing the system to be controlled by applying different potentials, a computer controlling the software in which the data are recorded and processed, a graphite working electrode functioning as an anode, a reference electrode controlling the potential difference on the graphite working electrode, a counter electrode functioning as a cathode, and an electrolyte solution comprising phythalocyanine which is obtained simultaneously on the surface of the graphite working electrode and bonded to the graphite working electrode covalently and/or deposited in powder form by covalently bonding to the graphene in the solution, wherein the method comprises the following process steps:

- Preparing an electrolyte solution comprising a phthalocyanine compound desired to be obtained simultaneously on a surface of the graphite working electrode,
- Immersing the graphite working electrode into the electrolyte solution and making the electrical connections of the electrodes,
- Performing a positive potential scanning on the graphite working electrode at a certain scan rate and recording the current,
- Realizing an oxidation reaction at a positive potential when switching from the negative zone to the positive zone during potential scan, i.e. in the anodic zone,
- Converting the graphite working electrode into the graphene oxide by the oxidation reaction occurring in the anodic zone,
- Continuing the scan at the negative potential by returning from the positive potential zone and recording the current,
- Converting the graphene oxide into the graphene by a reduction reaction occurring in the cathodic zone with a negative potential scan,
- Bonding the phthalocyanine compound to the graphene covalently in a potential working range scanned simultaneously and enhancing the bonding during the ongoing cycles, Obtaining the covalently bonded phthalocyanine-graphene hybrid material obtained based on the applied potential range on the electrode surface, or depositing the same in the solution in powder form, Immersing the electrode, the surface of which has the covalently bonded phthalocyanine-graphene hybrid material prepared as an electrode, into ultra pure water and washing the same, and drying at room temperature (18° C.-30° C.), Washing the covalently bonded phthalocyanine-graphene hybrid material prepared as powdery material directly with the ultra pure water and drying at a temperature of 20° C.-100° C.

In the phthalocyanine-graphene hybrid material production method, the basic process steps of which are given above in a chronological order, optionally, the covalently bonded phthalocyanine-graphene hybrid material obtained depending on the potential range during application may be obtained on the electrode surface. In this application, the electrode, the surface of which has the covalently bonded phthalocyanine-graphene hybrid material prepared as an electrolyte, is immersed into ultra pure water, washed, and dried at room temperature (18° C.-30° C.). As it is understood, as no chemicals are used, washing process is performed only with pure water without a need for an extra purification process. In addition, it is dried at room temperature without a need for high temperatures, and the energy requirement is indirectly reduced.

As a second option, the covalently bonded phthalocyanine-graphene hybrid material obtained depending on the potential range during application may be deposited in solution in powder form. In this application, the covalently bonded phthalocyanine-graphene hybrid material prepared as powder is washed directly with the ultra pure water and dried at a temperature of 20° C.-100° C.

The main difference in obtaining two different materials as a result of the hybrid material formation on the electrode surface and the production of the hybrid material in powder form is that the applied potential gap and the number of cycles are different. The potential scan applied for the covalently bonded phthalocyanine-graphene hybrid material prepared as an electrode is in the range of (−2.0 V) and (+4.0 V), while the number of the applied varying cycle is in the range of 1-200 (the number of the consecutively recorded alternating voltammograms). The potential scan applied for the covalently bonded phthalocyanine-graphene hybrid material prepared as a powdery material is in the range of (−3.0 V) and (+6.0 V), while the number of the applied varying cycle is in the range of 1-500 (the number of the consecutively recorded alternating voltammograms). The material formed on the electrode surface is poured into a support electrolyte solution medium in powder form with the applied overpotential ((−3.0 V) and (+6.0 V)) and the enhanced number of cycles (varying number of cycles in the range of 1-500). Thus, the powdery material is produced. In case of lower potential scan ((−2.0 V) and (+4.0 V)) and number of cycles (varying number of cycles in the range of 1-200), the phthalocyanine compound is covalently bonded to the structure simultaneously with the graphene formation, so that a hybrid material is formed on the electrode surface.

Therefore, in an embodiment of the invention, the potential scan in the graphite electrode is performed in the range of ((−3.0 V)−(+6.0 V)) at a scan rate in the range of 0.001 V/s−1.0 V/s and the number of cycles is in the range of 1-500, in order to prepare the covalently bonded phthalocyanine-graphene hybrid material as a powdery material.

Therefore, in another embodiment of the invention, the potential scan in the graphite electrode is performed in the range of ((−2.0 V)−(+4.0V)) at a scan rate in the range of 0.001 V/s−1.0 V/s and the number of cycles is in the range of 1-200, in order to prepare the electrode present on the surface of the covalently bonded phthalocyanine-graphene hybrid material.

In the method of at least one embodiment of the invention, a graphene based electrode is used as a working electrode, Ag/AgCl, calomel and/or $Hg/HgSO_4$ are used as a reference electrode, and a platinum (Pt) electrode is used as a counter electrode.

In the method for producing a phythalocyanine-graphene hybrid material according to at least one embodiment of the invention, the electrolyte solution is prepared from an acid solution selected from a group consisting of mono-protic and poly-protic acids, salts and bases in a concentration range of 0.0001 M-5.0 M and soluble phthalocyanine compounds having different functional groups at a concentration range of 0.000001 M-3.0 M. In the method, the electrolyte solution is preferably prepared from an acid solution in a concentration range of 0.001 M-5.0 M and soluble phthalocyanine compounds having different functional groups in a concentration range of 0.000001 M-1.0 M.

The acids used in the method of at least one embodiment of the invention are one or more acids selected from HCl, $HNO_3$, $H_2SO_4$, $H_3PO_4$, $H_3BO_3$, $HClO_4$, the bases are one or more bases selected from NaOH, KOH, $NH_4$, $Na_2CO_3$, the salts are one or more salts selected from KCl, NaCl, $LiClO_4$, $K_2HPO_4$, $KH_2PO_4$, $Na_2HPO_4$, $NaH_2PO_4$, $Na_2SO_4$.

The phthalocyanine compounds are macrocyclic molecules. The compounds without any substituted group (i.e. without any soluble functional groups) have quite low solubility. These compounds become soluble in water and organic solvents by attaching —R groups comprising different functional groups to the phthalocyanine ring having low solubility. These —R groups are functional groups containing groups, such as —OH, —COOH, —$SO_3$, $NH_2$, alkyl and alkoxy groups, long chain alkyl groups, ether groups, thioazole groups. In the method of at least one embodiment of the invention, the phthalocyanine compounds having functional groups with —R groups as specified herein are used.

In an exemplary application of the production method of the phthalocyanine-graphene hybrid materials of at least one embodiment of the invention, the following process steps are applied:

Preparing a solution system by adding a phthalocyanine compound (soluble phthalocyanine compounds having different functional groups) in a concentration range of 0.000001 M-3.0 M to the acid solutions having predetermined concentrations (solutions consisting of mono-protic and poly-protic acids, salts and bases) as an electrolyte, immersing the graphite working electrode into an electrochemical production system with an electrode, and making electrical connections of the electrodes, Performing a predetermined positive potential scan ((−3.0 V)−(+6.0 V)) on the graphite electrode at a predetermined scan rate (0.001 V/s−1.0 V/s) and recording the current, Realizing an oxidation reaction at a positive potential when switching from the negative zone to the positive zone during potential scan, i.e. in the anodic zone, Converting the graphite electrode into the graphene oxide by the oxidation reaction occurring in the anodic zone, Upon oxidation reaction in the anodic zone, continuing the scan at the negative potential by returning from the positive potential zone and recording the current, Converting the graphene oxide into the graphene by a reduction reaction in the cathodic zone with a negative potential scan, Bonding the phthalocyanine compound to the graphene covalently in a potential working range scanned simultaneously and enhancing the bonding during the ongoing cycles, Obtaining the covalently bonded phthalocyanine-graphene hybrid material obtained based on the applied potential range on the electrode surface when desired, and depositing the same in the solution in powder form, Immersing the electrode prepared as an electrode and having the covalently bonded phthalocyanine-graphene hybrid material on the surface thereof into ultra pure water and washing the same, and drying at room temperature, Washing the covalently bonded phthalocyanine-graphene hybrid material prepared as powder directly with the ultra pure water and drying at a temperature of 20° C.-100° C.

The most important advantage of at least one embodiment of the inventive method is the simultaneous production of the phthalocyanine-graphene hybrid material on the surface of the graphite electrode. Also, the electrode containing the covalently bonded graphene and phthalocyanine hybrid material obtained simultaneously on the surface of the graphite electrode allows to obtain a powdery material by depositing it in the solution medium thanks to the applied potential and the number of cycles.

Another advantage provided by the method of at least one embodiment of the invention is washing the powdery and electrode materials produced with ultra pure water during the washing process.

Some novel (specific) characteristics of at least one embodiment of the invention are simultaneous covalent attachment of the phthalocyanine compound to the structure during the formation of the graphene based materials by starting the scan process in the potential working range scanned on the surface of the graphite electrode, and provision of the electrode or powdery forms of the hybrid material as desired in a controlled manner depending on the number of cycles, period of time applied, and the potential and current range applied.

The invention claimed is:

1. A method for producing a phythalocyanine-graphene hybrid material in one step in which an electrochemical cyclic voltammetry system comprising a potentiostat allowing the system to be controlled by applying different potentials, a computer controlling the software in which the data are recorded and processed, a graphite working electrode functioning as an anode, a reference electrode controlling the potential difference on the graphite working electrode, a counter electrode functioning as a cathode, and an electrolyte solution comprising phythalocyanine which is obtained simultaneously on the surface of the graphite working electrode and bonded to the graphite working electrode covalently and/or deposited in powder form by covalently bonding to the graphene in the solution, the method comprising:

preparing an electrolyte solution comprising a phthalocyanine compound desired to be obtained simultaneously on a surface of the graphite working electrode, immersing the graphite working electrode into the electrolyte solution and making electrical connections of the electrodes, performing a positive potential scanning on the graphite working electrode at a certain scan rate and recording the current, realizing an oxidation reaction at a positive potential when switching from the negative zone to the positive zone during the potential scan, i.e. in the anodic zone, converting the graphite working electrode into the graphene oxide by the oxidation reaction occurring in the anodic zone, continuing the scan at the negative potential by returning from the positive potential zone and recording the current, converting the graphene oxide into the graphene by a reduction reaction occurring in the cathodic zone with a negative potential scan, bonding the phthalocyanine compound to the graphene covalently in a potential working range scanned simultaneously and enhancing the bonding during the ongoing cycles, obtaining the covalently bonded phthalocyanine-graphene hybrid material obtained based on the applied potential range on the electrode surface, or depositing the same in the solution in powder form, immersing the electrode, the surface of which has the covalently bonded phthalocyanine-graphene hybrid material prepared as an electrode, into ultra-pure water and washing the electrode, and drying at room temperature (18° C.-30° C.), washing the covalently bonded phthalocyanine-graphene hybrid material prepared as powder directly with the ultra-pure water and drying at a temperature of 20° C.-100° C.

2. The method for producing a phythalocyanine-graphene hybrid material in one step according to claim 1, wherein the working electrode is a graphite-based electrode.

3. The method for producing a phythalocyanine-graphene hybrid material in one step according to claim 1, wherein the reference electrode is an Ag/AgCl, calomel and/or $Hg/HgSO_4$ electrode.

4. The method for producing a phythalocyanine-graphene hybrid material in one step according to claim 1, wherein the counter electrode is a platinum electrode.

5. The method for producing a phythalocyanine-graphene hybrid material in one step according to claim 1, wherein the electrolyte solution is prepared from an acid solution selected from a group consisting of: mono-protic and polyprotic acids, salts and bases in a concentration range of 0.0001 M-5.0 M, and soluble phthalocyanine compounds having different functional groups at a concentration range of 0.000001 M-3.0 M.

6. The method for producing a phythalocyanine-graphene hybrid material in one step according to claim 5, wherein the electrolyte solution is prepared from an acid solution in a concentration range of 0.001 M-5.0 M and soluble phthalocyanine compounds having different functional groups at a concentration range of 0.000001 M-1.0 M.

7. The method for producing a phythalocyanine-graphene hybrid material in one step according to claim 5, wherein the acid solution is selected from one or more acids selected from the group consisting of: HCl, $HNO_3$, $H_2SO_4$, $H_3PO_4$, $H_3BO_3$, $HClO_4$, or one or more bases selected from NaOH, KOH, $NH_4$, and $Na_2CO_3$, or one or more salts selected from KCl, NaCl, $LiClO_4$, $K_2HPO_4$, $KH_2PO_4$, $Na_2HPO_4$, $NaH_2PO_4$, and $Na_2SO_4$.

8. The method for producing a phythalocyanine-graphene hybrid material in one step according to claim 5, wherein the phthalocyanine compounds having different functional groups are selected from phthalocyanine compounds comprising functional groups selected from the group consisting of: —OH, —COOH, —$SO_3$, $NH_2$, alkyl and alkoxy groups, long chain alkyl groups, ether groups, and tiazole groups.

9. The method for producing a phythalocyanine-graphene hybrid material in one step according to claim 1, further comprising performing a potential scan ((−2.0 V)−(+4.0V)) on the graphite electrode at a scan rate in a range of 0.001 V/s−1.0 V/s in order to prepare an electrode having the covalently bonded phthalocyanine-graphene hybrid material on the surface thereof.

10. The method for producing a phythalocyanine-graphene hybrid material in one step according to claim 1, wherein the number of cycles is in the range of 1-200 in order to prepare an electrode having the covalently bonded phthalocyanine-graphene hybrid material on the surface thereof.

11. The method for producing a phythalocyanine-graphene hybrid material in one step according to claim 1, further comprising performing a potential scan ((−3.0 V)−(+6.0 V)) on the graphite electrode at a scan rate in a range of 0.001 V/s−1.0 V/s in order to prepare the covalently bonded phthalocyanine-graphene hybrid material as a powdery material.

12. The method for producing a phythalocyanine-graphene hybrid material in one step according to claim 1, wherein the number of cycles is in the range of 1-500 in order to prepare the covalently bonded phthalocyanine-graphene hybrid material as a powdery material.

* * * * *